United States Patent [19]

Qu et al.

[11] Patent Number: 5,547,956
[45] Date of Patent: * Aug. 20, 1996

[54] PHARMACEUTICAL COMPOSITION AND THE METHOD FOR TREATING DRUG ADDICTS' WITHDRAWAL SYNDROMES AND DETOXIFYING ADDICTS BY THE SAME

[75] Inventors: Yueqian Qu, 510 Huayu Building, 15 Weiyuan Avenue, Chengguan Dist., Lanzhou, Gansu Province 730000, China; Peng Qu, Lanzhou, China

[73] Assignee: Yueqian Qu, Gansu Province, China

[*] Notice: The portion of the term of this patent subsequent to Mar. 1, 2011, has been disclaimed.

[21] Appl. No.: 125,363

[22] Filed: Sep. 22, 1993

Related U.S. Application Data

[63] Continuation-in-part of Ser. No. 912,791, Jul. 13, 1992, Pat. No. 5,290,784.

[30] Foreign Application Priority Data

Jul. 18, 1991 [CN] China ............... 91 104 811.1

[51] Int. Cl.$^6$ ........................ A61K 31/44
[52] U.S. Cl. ............ 514/279; 514/289; 514/810; 514/812
[58] Field of Search ............... 514/216, 279, 514/289, 810, 812

[56] References Cited

U.S. PATENT DOCUMENTS 5,290,784  3/1994  Qu et al. ................ 514/279

FOREIGN PATENT DOCUMENTS 2271059  4/1994  United Kingdom .

OTHER PUBLICATIONS

The Pharmacopeia of the People's Republic of China (1990) ED. pp. 304–306—Rotundine (L–Tetrahy–dropalmatine) and its preparation.
Studies on the Pharmacological Actions of Corydalis—Acts Physiologica Sinica—Kin Huo–Chang and Hsu Bin—pp. 150–157, vol. 21, No. 2 (1957).
TIPS—Mar. 87, vol. 8—Jin Guo–Zhang—Tetrahydropalmatine and its analogues as new dopamine receptor antagonists.
Fang Sheng–ding, et al: Studies on the Alkaloids of Stephanias Plants, II; Alkaloids of Stephania Viridiflavens H. S. Lo et M. Yang—Chinese Traditional and Herbal Drgus, vol. 12, No. 2, p. 1 (1981).
Cheng Gui–ren et al: Studies on the Alkoloids of Stephania Kwangsienis H. S. Lo et M. Yang—Chinese Traditional and Herbal Drugs, vo. 12, No. 4, p. 6 (1981).
The Merck Index—11th Edition (1989) p. 1452; 9147.
Chemical Abstracts—vol. 77, 1972, p. 209—111451g.
Chemical Abstracts—vol. 72, 1970, p. 492—43940k.
Chemical Abstracts—vol. 75, 1971, p. 89—85178k.
Yasuko Okamoto, et al: (1) Studies on the Alkaloids of Menispermaceous Plants, CCLXI; (2) Alkaloids of *Menispermum dauricum* DC (8)—Yakugaku Zasshi, vol. 91, No. 6, pp. 684–687 (1971).
The Merck Index—11th Edition (1989), p. 398; 2543.
Heihachiro Taguchi, et al: Studies on the Components of Cordalis spp. II, Alkaloids of *Corydalis ambigua* Cham.—Yakuguku Zasshi, vol. 83, No. 6, p. 578 (1963).
Chemical Abstracts—vol. 81, 1974, p. 291—166363t.
Chemical Abstracts—vol. 84, 1976, p. 298—147616y.
Chemical Abstracts—vol. 77, 1972, p. 214—85631u.
Chemical Abstracts—vol. 70, 1969, p. 79—93913h.
Helv. Chim. Acts—vol. 41, No. 29, pp. 335–343 (1959).
Chemical Abstracts—vol. 87, 1977, p. 25—15836x.
Chemical Abstracts—vol. 91, 1979, p. 32—32778e.
Pharmacological Study of Tetrahydropalmatine and its analogs—A new type of central depressants—B. Hsu and K. C. Kin—Arch. Int. Pharmacodyn. (1962).

*Primary Examiner*—Shean C. Wu
*Attorney, Agent, or Firm*—McAulay Fisher Nissen Goldberg & Kiel, LLP

[57] ABSTRACT

The invention relates to a pharmaceutical composition and a method for treating drug addicts' withdrawal syndrome and detoxifying addicts. The pharmaceutical composition comprises aconitane derivative of formulas I, II, their inorganic acid salts or mixtures thereof, and tetrahydroprotoberberine derivatives of formula II. The method of treatment comprises administering the pharmaceutical composition to drug addicts. The pharmaceutical composition of the present invention produces no drug dependence, excellent effects, fast action and low side-effects.

27 Claims, 1 Drawing Sheet

PHARMACEUTICAL COMPOSITION AND THE METHOD FOR TREATING DRUG ADDICTS' WITHDRAWAL SYNDROMES AND DETOXIFYING ADDICTS BY THE SAME

CROSS-REFERENCE TO RELATED APPLICATIONS

This application is a continuation-in-part of application Ser. No. 07/912,791 now U.S. Pat. No. 5,290,784 filed Jul. 13 1992, the contents of which are hereby incorporated by reference.

BACKGROUND OF THE INVENTION

This invention relates to a pharmaceutical composition containing the aconitane derivatives and the tetrahydroprotoberberine derivatives, and to a method for treating the withdrawal syndrome of drug addicts as well as detoxifying drug addicts.

As used herein, the terms:

"drug" means a substance which may cause addiction or dependence upon continuous use. Included within this term are drugs, such as, opium, morphine, heroine, cocaine, marijuana, as well as amphetamine, and the like;

"dependence" means a physical, physiological or psychological reaction and/or interaction of the drug and person, which results in the person exhibiting or having a forced or compulsive use of the drug without a recognized purpose or need for treating a disease, but rather for the purpose of achieving the desired effect, and/or to avoid withdrawal symptoms as defined hereinafter, which occur when the drug is discontinued or the amount used is reduced;

"withdrawal syndrome" means the symptoms and/or indications exhibited by persons who have dependence on a drug which occur on cessation of such use, and include symptoms, such as, perspiration, lacrimation, yawing, chilling, getting goose flesh, mydriasis, vomiting, diarrhea, abdominalgia, arrbythmia, blood pressure increase, insomnia, furor, tremor and delirium, and the like.

It is reported that there are 50 million drug addicts in the world, and the total volume of drug trade is estimated at about 5 billion U.S. dollars per year. On one hand, drug abuse results in serious damage to the human psyche and body, such as, in the loss of moral integrity, decrease in health level, life shortening, serious withdrawal syndrome after discontinuing drugs, and life endangerment. On the other hand, drug abuse also results in social unstability because the drug addict acts unscrupulously to get drugs and thus become a main source of serious crimes in the world. Consequently, drug abuse has seriously imperiled the progress and safety of human beings. To fight against the detrimental effects of drug abuse, governments all over the world take harsh measures to strictly prohibit drug abuse. However, this problem is getting worse. Therefore, it is very urgent for the world to have a medication and method with improved cure effects and low side effects in order to control and treat drug addiction.

At present, there are three major methods of treatment for addiction in most countries as follows:

1. Gradually Reducing Regimen

The main ingredient of the medication used in this method is dosing a medicament with decreasing amounts of opium. The opium content is decreased gradually at different stages of the treatment until it is zero.

2. Substitution Method

The analgesic methadone is used to treat the drug addict in this method.

3. Therapeutic Use of Other Drugs

There are also some medications used to treat drug addiction, such as, Buprenorphine, Clonidine, Cydazocine, Dihydroetorphine hydrochloride, and the like. However, some of these medications can easily cause nervous derangement and agitation, others will cause the withdrawal syndrome or the syndrome will appear on stopping the administration of the medication.

Clinical practice shows that there are very serious drawbacks in the above three treatments for drug addiction. For example, the regimen of gradually reducing the opium content, requires long periods of treatment. Furthermore, this method cannot result in the drug addicts' fundamentally getting rid of this dependency on drugs, and the proportion of re-abusing after treatment still is high.

In the substitution method, methadone is an analgesic and may also result in drug dependence. For example, the dependence potential of 100 mg of oral methadone is equivalent to that of 10 mg of injected morphine. Also, methadone itself has many side effects, such as, pneumonectasis, immunologic symptoms, impotency, as well as accumulation of the drug in the body leading to intoxication, and, more seriously, blindness in both eyes. Infants born by mothers addicted to methadone are likely to show withdrawal symptoms.

In the other drug therapy described above, the medications may have adverse side effects and some of them may also cause drug dependence. At present, some medications are being tested to treat drug addiction, such as, Abbott 69024, Amantidine, Bupropion, Buprenorphine, Bromocriptine, Buspirone, Carbamazepine (Tegretol), Fluoxetine (Prozac), Flupenthixol, Gepirone, Laam, Mazindol, Naltrexone and Schering 23390 (see ref. Scientific American, Mar. 1991, pp 71–79). A few of them have been proved ineffective and others are under development. Thus, there is an urgent need of drug independence medication having high curative effects and low side effects for the treatment of drug addiction.

SUMMARY OF THE INVENTION

An object of this invention is to provide a pharmaceutical composition to treat drug addiction and a treatment method which avoids drug dependence and with high curative effects and low side effects.

The inventor has discovered that a pharmaceutical composition containing the aconitane derivatives which have the structures of formula I or II, or their inorganic acid salts, and the tetrahydroprotoberberines which have the structure of formula III or their inorganic acid salts and combinations thereof, possess excellent effects of treatment addiction without drag dependence.

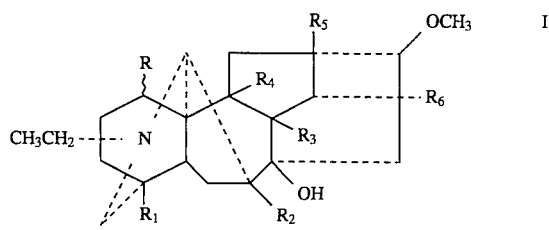

3
-continued

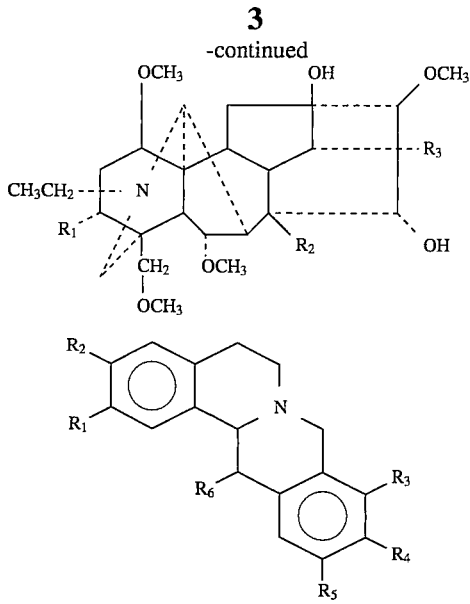

In formula I, R =αOCH$_3$, αOH or αOCH$_3$, R$_1$=OAcABz, OH, OABz or H, R$_2$=H or OH, R$_3$=H or OH, R$_4$=H or OH, R$_5$=H or OH, R$_6$=OCH$_3$, OBz, OAc or OH.

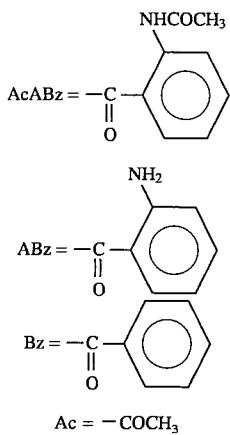

In formula II, R$_1$=R$_2$=R$_3$=OH.

In formula III, R$_1$=OCH$_3$ or OH, R$_2$=OCH$_3$, R$_3$=OCH$_3$ or H, R$_4$ =OCH$_3$ or OH, R$_5$=H or OCH$_3$, R$_5$=H or CH$_3$.

Treating the drag addicts with the pharmaceutical composition of the invention, containing the aconitane derivatives having the structures of formula I and/or II or their inorganic acid salts and the tetrahydroprotoberberine derivatives having the structures of formula III or their inorganic acid salts, can relieve the drug dependence and completely cure the withdrawal syndrome within 3 to 4 days. The inventive pharmaceutical composition does not produce drug dependence and exhibits low side effects.

Treatment of drug addicts with this pharmaceutical composition can relieve the drug addicts of dependence upon drugs, treat the withdrawal syndrome which results from discontinuing use of the drugs, and produces no dependence on the treating composition and low side effects.

BRIEF DESCRIPTION OF THE DRAWING

The drawing is a graph showing weight variation with time for Examples 1 and 2 hereof.

DETAILED DESCRIPTION OF THE INVENTION

Figure 1:
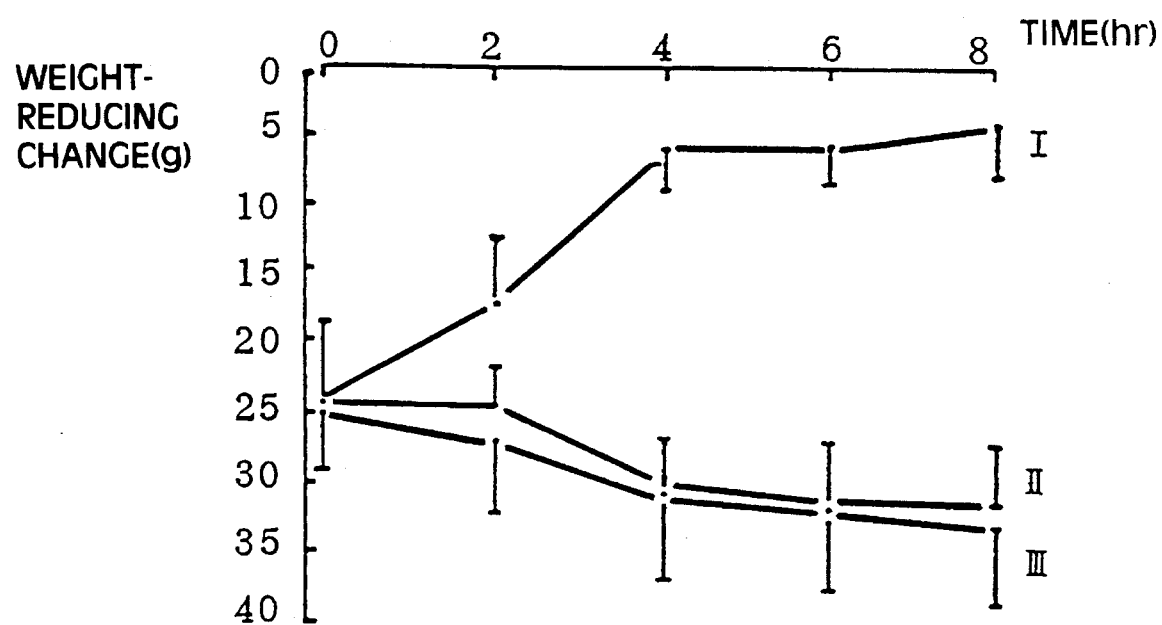

According to this invention, the inventive pharmaceutical composition may contain or may not contain anticholinergic agents, such as, scopolamine hydrobromide, anisodamine hydrobromide, and the like, as well as pharmaceutically acceptable excipients. Preferred aconitane derivatives include lappaconitine hydrobromide, lappaconine hydrobromide, N-deacetyl-lappaconitine hydrobromide, the total alkaloids of Aconitum sinomontanum Nakai. Preferred tetrahydroprotoberberine derivatives having the structure of formula III or their inorganic acid salts are the 1-tetrahydropalmatine, dl-tetrahydropalmatine sulfate, and stepholidine hydrobromide. The preferred anticholinergic agents are scopolamine hydrobromide and anisodamine hydrobromide. Particularly good effects are achieved when the pharmaceutical composition contains anticholinergic agents.

Preferred inventive compositions are:

1. The formulation including lappaconitine hydrobromide and 1-tetrahydropalmatine or dl-tetrahydropalmatine sulfate or stepholidine hydrobromide, scopolamine hydrobromide and/or anisodamine hydrobromide as well as a conventional pharmaceutical excipient.

2. The formulation containing lappaconine and 1-tetrahydropalmatine or dl-tetrahydropalmatine sulfate or stepholidine hydrobromide, scopolamine hydrobromide and/or anisodamine hydrobromide as well as a conventional pharmaceutical excipient.

3. The formulation including N-deacetyllappaconitine hydrobromide and 1-tetrahydropalmatine or dl-tetrahydropalmatine sulfate or stepholidine hydrobromide, scopolamine hydrobromide and/or anisodamine hydrobromide as well as a conventional pharmaceutical excipient.

4. The formulation including the total alkaloid hydrobromides of Aconitum sinomontanum and 1-tetrahydropalmatine or dl-tetrahydropalmatine sulfate or stepholidine hydrobromide, scopolamine hydrobromide and/or anisodamine hydrobromide as well as a conventional pharmaceutical excipient.

According to this invention, the pharmaceutical composition of this invention can be used in the form of a tablet, powder, capsule or administered by injection. The form of tablet or capsule is preferred.

This invention also provides a method for the treatment of drug-addicts' withdrawal syndrome and detoxification of drug addicts, which comprises administering an anti-withdrawal syndrome or detoxification effective amount of the pharmaceutical composition of this invention to the drug addicts. The administration route of the inventive composition can be oral, subcutaneous injection, intramuscular injection, intravenous instillation, and the like. Oral administration is preferred. In the treatment by oral administration route, the dosage is generally 0.05~0.25 mg/kg/per time of aconitane derivatives of formula I or II or their inorganic acid salts, 1–2.5 mg/kg/per time of tetrahydroprotoberberine or its inorganic acid salt, 0.00033~0.005 mg/kg/per time of scopolamine hydrobromide, and/or 0.066~0.16 mg/kg/per time of anisodamine hydrobromide.

Generally, oral administration is given during the first four days, the inventive composition is given every 6 hours, 4 times a day, 2 tablets or 2 pills per time; during the following three days, the composition is given every 8 hours, 3 times a day, 2 tablets or pills per time.

The following examples illustrate the invention:

I. Addiction Test of Lappaconitine Hydrobromide

1. Mouse Jumping Test

Male mice weighing 18–22 g were used for the test and divided into 3 groups (10 for every group). The first group of mice was given a subcutaneous injection in a dose of 80 mg/kg morphine hydrochloride every day for 20 days. The second group of mice was given a subcutaneous injection of lappaconitine hydrobromide (8 mg/kg) for 20 days. The third group was a control group and was given physiological saline. 6 hours after being given the last dose, all the mice were given an intraperitoneal injection of 10 mg/kg allyl dromaran, and then were placed in a cone cylinder cage (diameter=30 cm, height=35 cm). The number of jumps for each mouse in 60 minutes was recorded. The mice of the first group after administrating morphine looked excited, frequently ran around and showed obvious pilo-erection reaction. The mice of the group also showed an obvious jumping reaction after injection of allyl dromaran. The mice of the second group after administrating lappaconitine hydrobromide looked quiet and immobile and showed no pilo-erection reaction. After the injection of allyl dromaran they showed no jumping reaction.

In another case, male mice weighing 18–22 g were divided into four groups (10 for every group). Two groups of mice were injected subcutaneously with lappaconitine hydrobromide 7 times within 2 days. The initial dosage was 3.5 mg/kg. Then, additional doses of 0.5 mg/kg and 1.0 mg/kg were given for every injection in each group, respectively. The third group of mice was injected subcutaneously with morphine hydrochloride 7 times within 2 days. The initial dosage was 2.5 mg/kg and an escalating dose schedule of 5, 10, 20, 30, 40, 50 mg/kg was applied. The fourth group of mice was used as control group and was given physiological saline. Two hours after the last injection, all the mice of the above four groups were injected with 50 mg/kg nalorphine through the intraperitoneal cavity. The number of jumps within 10 minutes in each group of mice were recorded. The data obtained is summarized in Table 4.

The test result in Table 4 shows that lappaconitine hydrobromide obviously differs from morphine hydrochloride, and the former does not cause drug dependence.

2. Substitution Test on Weight Reducing of Morphine-dependent rats.

Wister male rats weighing 200–250 g were divided into 3 groups (10 for each group). All three groups were given subcutaneous injections of 25 mg/kg morphine hydrochloride twice a day. The injections lasted for 12 weeks to cause the rats to become dependent upon morphine. After discontinuing the injections of morphine, the rats were suppressive and immobile, refusing food and losing weight (after 24 hours, the average weight loss per rat was 25 g). Then, the three groups of rats were injected with morphine, lappaconitine, and physiological saline, respectively. The weight changes of the rats were observed and recorded in FIG. 1.

Notes for FIG. 1:

Abscissa-time(hr): 24 hours after stopping the injection of morphine for three groups of rats, and injecting them subcutaneously with morphine, lappaconitine and physiological saline, respectively, the average weight change of the rats within 8 hours in each group were recorded. The 24th hour after stopping of the injection of the morphine is assumed to be zero.

Ordinate- weight of rats: The average weight lost of the three groups of rats at the 24th hour after stopping the injection of morphine, and the average weight change in 8 hours in each group after 24 hours of injection with morphine, after the rats were given injections of morphine, physiological saline and lappaconitine, respectively. In the test, the average weight before stopping injection of morphine is assumed to be zero.

I Morphine hydrochloride 25 mg/kg. sc
II Physiological saline 2 ml/kg. sc
III Lappaconitine hydrobromide 8 mg/kg. sc FIG. 1 shows that the group of rats which were injected with morphine turned to being excited from being suppressive, moved increasingly, frequently took food and water, and the weight increased to the level shown very quickly before stopping injection of morphine. FIG. 1 also shows that the group of rats which were injected with lappaconitine still looked suppressive and no weight increase was observed. The test results indicated that lappaconitine did not act as a substitution for morphine.

3. Monkey addiction test

Three of 6 Macaca mulatta weighing 2.75–4.75 kg were subcutaneously injected with lappaconitine twice a day. The initial dosage is 0.1 mg/kg, and the dose was successively escalated to the maximum tolerance dosage, 2 mg/kg within 50 days. Then, the tolerance dosage was maintained to the 53rd day, 67th day and 92nd day, respectively. The total injection dosages for the three monkeys were 196, 400 and 635 mg, respectively. On day 63 and day 92, the injections of lappaconitine to the monkeys was stopped. During the following 24 hours, the monkeys had no different behavior and appetite from that before stopping injection. On day 29, 53, 59, 67 and 90, injections to the monkeys were discontinued and after 18 hours, subcutaneous injection of nalorphine (4 or 8 mg/kg) were given. No withdrawal symptoms were observed.

Another three monkeys were given subcutaneous injection of morphine twice a day. The initial dosage was 2.5 mg/kg, and the dosage was successively increased to 25 mg/kg on day 21. Then, this dosage was maintained until the 30th day, and the monkeys showed dependence on morphine. 18 hours after stopping the injection of morphine, the monkeys showed obvious withdrawal syndrome, such as, agitation and restlessness, turning, sometimes lying on the side or on the bottom of the cage, scratching, chain biting, crying, vomiting, shivering, paroxysmal tremor, and the like. At that time, if a subcutaneous injection of nalorphine was given to the monkeys, the above symptoms would be more obvious. After subcutaneous injection of morphine to the monkeys, the above withdrawal symptoms were obviously reduced or disappeared in 3–5 minutes. A subcutaneous injection of 2 mg/kg lappaconitine could not relieve or weaken the above withdrawal symptoms. This indicates that lappaconitine does not act as a substitute for morphine. The above test results are shown in Table 5.

The above test results also indicate that lappaconitine, unlike morphine, does not cause dependence after long term use.

II. Toxicity Test

1. Acute Toxicity Test

Healthy mice weighing 18–22 g were given toxicity dosages of lappaconitine through intra gasteria, subcutaneous injection and intravenous injection, and then showed toxicity reactions, such as, paroxysmal restlessness, and foreleg tic. When given a lethal dosage, the mice showed paroxysmal convulsion, respiration suppression until suffocation, and death. The LD50 values (95 % confidence limit) for, intra gasteria, subcutaneous injection and intravenous injection were 32.4 (25.9–40.5), 11.7 (9.2–14.9) and 8.4 (7.2–9.7) mg/kg, respectively. After being given intraperitoneal injection of toxicity dosage of lappaconitine, rats looked suppressive and immobile lying on stomach in cage, obvious suppression of respiration and showed convulsions before death. The LD50 for lappaconitine was 16.5 (15.0–18.1) mg/kg.

Two Macca Mulatta were given subcutaneous injections of 2 mg/kg lappaconitine. No toxic reaction and no effect on electrocardiography were observed. 30 minutes after being given subcutaneous injection of 3 mg/kg lappaconitine, the monkeys showed restlessness, slobbering, increased swallowing, drooping eyelids, and rigidity of leg muscles. After 45 minutes, one monkey increased restlessness, and further developed convulsion. During convulsion its respiration stopped, and was recovered with artificial respiration. The convulsion still continued until death after 1 hr. Another monkey did not give signs of convulsion, and the above toxic reaction lasted for 2 hours and then disappeared. Electrocardiography examination indicated that T wave had elevation, T wave and P wave fused, and R wave became smaller and notching. Next day, the electrocardiography examination indicated that the monkey was normal.

2. Subacute toxicity Test

Ten Wister rats weighing 200–250 g were divided into 2 groups (5 for each group). Each group was given intraperitoneal injection of 5 mg/kg or 10 mg/kg of lappaconitine a day, respectively. The injection was continued for 30 days. 5 wister rats of a control group were given subcutaneous injections of saline (2 ml/kg). Compared to the control group, the medicated groups of rats showed inhibited weight increase at different levels. No obvious change was observed in electrocardiography examination. No change was observed during tests of the hepatic and renal function (GPT, zinc sulfate turbidity test, urea nitrogen, creatinine) and histological and pathological examination of different viscera.

Another ten Wister rats were medicated with successively escalated doses, in other words, the rats were first injected with lappaconitine (8 mg/kg) intraperitoneally. After one week with 10 mg/kg; after 2 weeks with 12 mg/kg; after 16 days with 14 mg/kg; and the last dose was maintained until day 28. The test results indicated that the weight increase of the medicated group of rats was a little suppressed, compared to the control group. The histological and pathological examination of all viscera indicated similar results to the control group, except a little myocardial edema and hydropic degeneration.

Three Macca Mulatta weighing 2.75–4.75 kg were injected with lappaconitine subcutaneously twice a day. Initiated with 0.1 mg/kg, the dosage was increased successively to the highest tolerated dosage, 2 mg/kg within 50 days, and the last dosage was maintained to day 53, day 67 and day 92, respectively. The accumulated injective dosage was 196, 400 and 635 mg, respectively. No toxic reaction for the monkeys was observed during the administration process. No obvious change appeared during the continuous electrocardiographic examination. Histological and pathological examinations mainly indicated stimulating reaction, except a little edema and hydrodenaturation in the liver and increasing cerebral colloid cells.

III. A Treatment Test For Mice Dependent on Morphine or Cocaine

Male mice weighing 18–22 g were injected subcutaneously with morphine (100 mg/kg) twice a day, and the injection was continued for 8 days. 6 hours after the last dose, the mice were injected with nalorphine (50 mg/kg). The mice showed frequent movement, attacking reactions and jumping reactions. The jumping reaction was most vigorous within the first 30 minutes. Based on the jumping reactions of the mice, those morphine-dependent mice whose jumping number within 30 minutes was more than 60% of the average jumping number, were selected and divided at random into 8 groups of 10 mice each.

A seven-day treatment to relieve morphine-dependence was conducted based on the medications, the dose and administration route listed in Table 6 for each group of mice which were morphine-dependent. In the first 4 days, administration was given once per 6 hours, four times a day. From day 5 through day 7, administration was given once every 8 hours, three times a day. On day 5 and day 8 of treatment, respectively, subcutaneous injections of nalorphine (50 mg/kg) were made to induce addiction. The test results indicated that each group of mice gave a negative reaction against nalorphine except the control group of morphine dependent mice, most of which died during seven days of subcutaneous injection of saline. During the 3-day observation following after stopping the treatments, the mice treated did not show withdrawal symptoms. Even when nalorphine (50 mg/kg) was injected subcutaneously, the mice did not exhibit withdrawal symptoms either. The results are listed in Table 6.

In the same way as described above, subcutaneous injection of cocaine (10 mg/kg) were given to the mice twice a day, and the injection was continued for 7 days. During this period of injection of cocaine, the mice gave abnormal signs such as anorexia, pilo-erection, and frequent walking with holding tail, and the like. After treatment with lappaconitine, the mice recovered to normal.

IV. Clinic Treatment Tests

Case 1

A 29 year old male addict had taken heroine for about 4 years. The pharmaceutical composition of medications of this invention were administered to him before he showed withdrawal symptoms. In the first day after administration, the addict did not show withdrawal symptoms, except for intermittent perspiration. In the second day of treatment, the addict showed withdrawal symptoms, such as, light perspiration, yawing, lacrimation, mydriasis, and the like, as well as vomiturition once, diarrhoea once, light* elbow ache lasting intermittently about 16 hours and somewhat serious** palpitations lasting intermittently about 4 hours. However, the addict had normal sleep and diet. The above withdrawal symptoms disappeared in the evening of the second day and did not reappear. He is cured.

Case 2

A 27 year old male addict had taken heroine for about 6 years. The pharmaceutical composition of this invention was administered to him before he showed withdrawal symptoms. In the first day after administration, the withdrawal symptoms did not appear until 10 hours after administration of the composition of the day. After 10 hours, the addict was observed to show withdrawal symptoms, such as, light yawing, raving in sleep, mydriasis and the like, as well as vomiturition once, abdominal pains twice and diarrhoeas. The withdrawal symptoms lasted 38 hours and included mainly intermittent light* palpitation, ache of shanks and arms, as well as somewhat serious** palpitation which lasted intermittently for 5 hours. The addict had normal sleep and diet. The above withdrawal symptoms disappeared at the 60th hour after administration and did not reappear. He was cured.

Case 3

A 29 year old male addict had taken heroine for about 5 years. The pharmaceutical composition of this invention was given to him before he was observed to show withdrawal symptoms. He was not observed to show the symptoms within 12 hours after administration. After 12 hours, the addict showed symptoms, such as, light palpitation, perspiration, mydriasis and the like, as well as vomiturition three times and diarrhoea twice, and light* or somewhat serious** aches of shanks and waist. The addict had normal sleep and diet. The above withdrawal symptoms disappeared totally and did not reappear at the 65th hours after administration. He was cured.

The above clinical test results demonstrated that the pharmaceutical composition of this invention to treat drug addiction does not cause drug dependence. It is effective to relieve drug dependence, to cure withdrawal symptoms and acts rapidly without side effects.

In the Tables, light* is marked as +, the manifestations demonstrated palpitation, aches of waist and legs told by addicts; lying and sitting; sometimes tossing and tumbling on bed; no pain in addicts face; sometimes having hours of sleep.

somewhat serious** is marked as ++, the manifestations demonstrated nervous walking back and forth in the room; or having aches of waist and legs, requirement for extending arms and legs, having pain on addicts face.

serious*** is be marked as +++, the manifestations demonstrated wild behavior; producing bloody behavior, such as bumping with head, persecution, etc. In the cases of treatment, a few addicts said that they felt unwell as if an insect was crawling within their arms and legs.

TABLE 1

The Composition of Formula I

| No. | Aconitane derivatives | Formula | MW | mp (°C.) |
|---|---|---|---|---|
| 1 | Lappaconitine | $C_{32}H_{44}N_2O_8$ | 584 | 224–225 |
| 2 | Lappaconine | $C_{23}H_{37}NO_6$ | 423 | 78–80 |
| 3 | N-Deacetyllappaconitine | $C_{30}H_{42}N_2O_7$ | 542 | 117–119 |
| 4 | Isolappaconitine | $C_{32}H_{44}N_2O_8$ | 584 | 198–200 |
| 5 | Deoxylappaconitine | $C_{32}H_{44}N_2O_7$ | 568 | 212–214 |
| 6 | neofinaconitrine | $C_{30}H_{42}N_2O_6$ | 526 | |
| 7 | Ranaconitine | $C_{32}H_{44}N_2O_9$ | 600 | 130–131 |
| 8 | Ranaconine | $C_{23}H_{37}NO_7$ | 439 | 105–107 |
| 9 | N-Deacetylranaconitine | $C_{30}H_{42}N_2O_8$ | 558 | 125–127 |
| 10 | Finaconitine | $C_{32}H_{44}N_2O_{10}$ | 616 | 220–221 |
| 11 | N-Deacetylfinaconitine | $C_{30}H_{42}N_2O_9$ | 574 | 121–123 |
| 12 | Puberanine | $C_{32}H_{44}N_2O_9$ | 600 | |
| 13 | Episcopalisine | $C_{29}H_{39}NO_6$ | 497 | |
| 14 | Episcopalisinine | $C_{22}H_{35}NO_5$ | 393 | 152–154 |
| 15 | Episcopalitine | $C_{24}H_{37}NO_5$ | 419 | |
| 16 | Delavaconitine | $C_{29}H_{39}NO_6$ | 497 | |
| 17 | Delavaconine | $C_{22}H_{35}NO_5$ | 393 | 152 |
| 18 | Aconosine | $C_{22}H_{35}NO_4$ | 377 | 142–143 |
| 19 | Scopaline | $C_{21}H_{33}NO_4$ | 363 | 167–169 |

| No. | aconitane derivatives | Specific Rotation | $R_1$ | $R_2$ |
|---|---|---|---|---|
| 1 | Lappaconitine | $[\alpha]_D^{25}$ 27.0°(C0.22,CHCl$_3$) | OAcABz | H |
| 2 | Lappaconine | | OH | H |
| 3 | N-Deacetyl-lappaconitine | $[\alpha]_D^{33}$ 39.9°(C1.5,CHCl$_3$) | OABz | H |
| 4 | Isolappaconitine | | OAcABz | OH |
| 5 | Deoxyl-appaconitine | | OAcABz | H |

TABLE 1-continued

The Composition of Formula I

| | | | | | |
|---|---|---|---|---|---|
| 6 | Neofinaconitine | | | OABz | H |
| 7 | Ranaconitine | $[\alpha]_D^{22}$ 40.2°(C0.19,MeOH) | | OAcABz | OH |
| 8 | Ranaconine | | | OH | OH |
| 9 | N-Deacetyl-ranaconitine | $[\alpha]_D^{26}$ 43.7°(C2.0,CHCl$_3$) | | OABz | OH |
| 10 | Finaconitine | $[\alpha]_D^{22}$ 44.7°(C0.1,Me OH) | | OAcABz | OH |
| 11 | N-Deacetyl-finaconitine | $[\alpha]_D^{10}$ 34.9°(C0.46,CHCl$_3$) | | OABz | OH |
| 12 | Puberanine | $[\alpha]_D^{20}$ 16.6°(C0.6,CHCl$_3$) | | OAcABz | OH |
| 13 | Episcopalisine | $[\alpha]_D^{21}$ –11.7°(C3.2,EtOH) | | H | H |
| 14 | Episcopalisinine | $[\alpha]_D^{26}$ –8.7°(C6.8,EtOH) | | H | H |
| 15 | Episcopalitine | $[\alpha]_D^{22}$ –0.90°(C14.0,EtOH) | | H | H |
| 16 | Delavaconitine | $[\alpha]_D^{17}$ –9.56°(C7.0,EtOH) | | H | H |
| 17 | Delavaconine | $[\alpha]_D^{15}$ –6.4°(C1.23,CHCl$_3$) | | H | H |
| 18 | Aconosine | $[\alpha]_D^{22}$ –25.4°(C4,Me OH) | | H | H |
| 19 | Scopaline | | | H | H |

| No. | $R_3$ | $R_4$ | $R_5$ | $R_6$ | R | Original Plant |
|---|---|---|---|---|---|---|
| 1 | OH | H | H | OCH$_3$ | αOCH$_3$ | Aconitum sinomontanum Nakai; A. finetianum Hand-Mazz |
| 2 | OH | H | H | OCH$_3$ | αOCH$_3$ | |
| 3 | OH | H | H | OCH$_3$ | αOCH$_3$ | A. finetianum Hand-Mazz |
| 4 | H | H | H | OCH$_3$ | αOCH$_3$ | A. finetianum Hand-Mazz |
| 5 | H | H | H | OCH$_3$ | αOCH$_3$ | A. finetianum Hand-Mazz |
| 6 | H | H | H | OCH$_3$ | αOCH$_3$ | A. finetianum Hand-Mazz |
| 7 | OH | H | H | OCH$_3$ | αOCH$_3$ | Aconitum sinomontanum Nakai; A. finetianum Hand-Mazz |
| 8 | OH | H | H | OCH$_3$ | αOCH$_3$ | |
| 9 | OH | H | H | OCH$_3$ | αOCH$_3$ | A. finetianum Hand-Mazz |
| 10 | OH | OH | H | OCH$_3$ | αOCH$_3$ | A. finetianum Hand-Mazz |
| 11 | OH | OH | H | OCH$_3$ | αOCH$_3$ | A. finetianum Hand-Mazz |
| 12 | OH | H | H | OCH$_3$ | βOCH$_3$ | A. barbatum var. puberulum |
| 13 | OH | H | H | OB$_z$ | αOCH$_3$ | A. episcopale Le'vl |
| 14 | OH | H | H | OH | αOCH$_3$ | A. episcopale Le'vl |
| 15 | H | H | H | OAc | αOCH$_3$ | A. episcopate Le'vl |
| 16 | H | H | OH | OB$_z$ | αOCH$_3$ | A. delavayi Franch |
| 17 | H | H | OH | OH | αOCH$_3$ | |
| 18 | H | H | H | OH | αOCH$_3$ | A. forestii Diels |
| 19 | H | H | H | OH | αOH | A. episcopale Le'vl |

TABLE 2

The Composition of Formula II

| Name | Formula | MW | mp (°C.) | Specific Rotation | $R_1$ | $R_2$ | $R_3$ | Original Plant |
|---|---|---|---|---|---|---|---|---|
| Aconine | $C_{25}H_{41}NO_9$ | 499 | 132 | $[a]_D$ + 23° | OH | OH | OH | |

TABLE 3

The compound of formula III

| No. | tetrahydro protoberberine derivatives | formula | MW | mp (°C.) | Specific Rotation | $R_1$ |
|---|---|---|---|---|---|---|
| 1 | l-tetrahydropal-matine | $C_{22}H_{25}NO_4$ | 355 | 144 | $[\alpha]_D^{26}$ −295°(C = 0.8,EtOH) | $OCH_3$ |
| 2 | dl-tetrahtdropal-matine | $C_{22}H_{25}NO_4$ | 355 | 148–149 | $[\alpha]_D 0°$ | $OCH_3$ |
| 3 | Stephoridine | $C_{19}H_{27}NO_4$ | 327 | 129–133 | $[\alpha]_D^{21}$ −263°(C = 0.337,MeOH) | OH |
| 4 | Corydaline | $C_{22}H_{27}NO_4$ | 369 | 135 | $[\alpha]_D^{20}$ +311°(C = 0.8,EtOH) | $OCH_3$ |
| 5 | Xylopinine | $C_{23}H_{25}NO_4$ | 355 | 181–182 | $[\alpha]_D^{15}$ −177.2°(C = 4.07,$CHCl_3$) | $OCH_3$ |

TABLE 4

Observation of jumping reaction for mice after subcutaneous injections of lappaconitine or morphine

| Given pharmaceuticals | Dosage (mg/kg) | Administration */day | Accumulated Total Dosage (mg/kg) | Number of mice given pharmaceuticals | Number of mice tested |
|---|---|---|---|---|---|
| Physiological saline | — | 2 | | 10 | 10 |
| | 2 | 20 | | 10 | 10 |
| Morphine | 2.5 | 2 | 157.5 | 10 | 10 |
| | 80 | 20 | 1600 | 10 | 10 |
| Lappaconitine | 3.5 | 2 | 35 | 10 | 10 |
| | 3.5 | 2 | 45.5 | 10 | 5** |
| | 8.0 | 20 | 160 | 18 | 18 |

| Given pharmaceuticals | mg/kg Nalorphine | ip allyl-dromaran | number of jumping mice | jumping times of each mouse |
|---|---|---|---|---|
| Physiological saline | 50 | | 0 | 0 |
| | | 10 | 0 | 0 |
| Morphine | 50 | | 7 | 9 |
| | | 10 | 9 | 34 |
| Lappaconitine | 50 | | 0 | 0 |
| | 50 | | 0 | 0 |
| | | 10 | 1 | 0.2 |

TABLE 4-continued

Observation of jumping reaction for mice after subcutaneous injections of lappaconitine or morphine

*Once a day for 20 days group; Five injections on first day and twice on the second day for the 2 day group.
**During the administration of the pharmaceuticals, five mice died of accumulated toxicity.

TABLE 5

Observation of the substitution role of lappaconitine in the withdrawal syndrome of morphine--dependent monkeys

| | | | Withdrawal Syndrome | |
|---|---|---|---|---|
| No. of monkeys | Injection of morphine (day) | accumulated total dosage (g) | 18 hr after stopping morphine | Nalorphine 0.5 mg/kg sc |
| 6 | 42 | 4.66 | + | |
| 7 | 40 | 3.56 | + | |
| | 62 | 6.59 | | + |
| | 69 | 7.56 | | + |
| | 91 | 10.97 | + | |
| 8 | 33 | 3.61 | | + |
| | 49 | 6.06 | + | |

Notes:
+ means symptoms present.
− means no symptoms.

TABLE 6

Observation of treatment for Morphine--dependent Mice

| Medication | Dosage mg/g (Administration route) | Days of Administration (time/hour) day | day | Accumulated Total Dosage (mg/kg) | Number of Mice morphine-dependent | Number of mice treatment |
|---|---|---|---|---|---|---|
| Saline | 10 ml/kg (sc) | 1/6 | 1/8 | 250 ml | 10 | 08 |
| Lappaconitine hydrobromide | 0.45 (sc) | 1/6 | 1/8 | 11.25 | 10 | 10 |
| Lappaconitine hydrobromide* | 0.225 (sc) | 1/6 | 1/8 | 5.63 | 10 | 10 |
| Scopolamine hydrobromide | 0.05 (sc) | | | | | |
| Lappaconitine hydrobromide | 0.45 | 1/6 | 1/8 | 11.2 | 10 | 10 |
| Scopolamine hydrobromide | 0.1 (sc) | | | 2.5 | | |
| Lappaconitin hydrobromide | 0.9 | 1/6 | 1/8 | 22.5 | 10 | 10 |
| Scopolamine hydrobromide | 0.2 (ig) | | | 5.0 | | |
| Lappaconitine | 0.45 | 1/6 | 1/8 | 11.25 | | |

TABLE 6-continued

Observation of treatment for Morphine--dependent Mice

| | | | | | | |
|---|---|---|---|---|---|---|
| hydrobromide Scopolamine hydrobromide | 0.1 (ig) | | | 2.5 | 10 | 10 |
| N-deacetyllapp-aconitine hydrobromide | 5 (sc) | 1/6 | 1/8 | 125 | 10 | 10 |
| Lappaconine hydrobromide (sc) | 5 (s) | 1/6 | 1/8 | 125 | 10 | 10 |

| Medication | Nalorphine mg/kg | Day 5 of treatment | Day 1 after stopping drug | Day 4 after stopping administration |
|---|---|---|---|---|
| Saline | 50 | 4/6** | 3/3** | 1/2** |
| Lappaconitine hydrobromide | 50 | 1/10* | 0/10 | 0/10 |
| Lappaconitine hydrobromide, Scopolamine hydrobromide | 50 | 1/10*4 | 1/10* | 1/10 |
| Lappaconitine hydrobromide, scopolamine hydrobromide | 50 | 0/10 | 0/9 | 0/9 |
| Lappaconitine hydrobromide, Scopolamine hydrobromide | 50 | 0/10 | 0/8 | |
| Lappaconitine hydrobromide, Scopolamine hydrobromide | 50 | 1/10*5 | 0/9 | 0/9 |
| N-deacetyllapp-aconitine hydrobromide | 50 | 0/10 | 0/10 | 0/10 |
| Lappaconine hydrobromide | 50 | 0/10 | 0/10 | 0/10 |

Note
*denotes a clinical prescription, but the scp is larger than clinic prescription.
**4/6 denotes six mice survived, of which four were jumping and the number of jumps of the four is 17, 14, 8 and 16. respectively; 3/3 means three mice survived, and the number of jumps of the three are 12, 10 and 9, respectively; 1/2 denotes that two mice being survived, and one jumped 7 times.
*3denotes that ten mice survived during the test, but only one jumped five times.
*4denotes that ten mice survived during test, and only one jumped 10, 6 and 1 times, on the fifth day of treatment, the eighth day of treatment and the fourth day, respectively, of stopping administration.
*5denotes that ten mice survived during the test, only one jumped 16 times.

What is claimed is:

1. A pharmaceutical composition comprising:

aconitane derivatives having the structure of formula I, II, their inorganic acid salts, and combinations thereof; and tetrahydroprotoberberine derivatives having the structure of formula III,

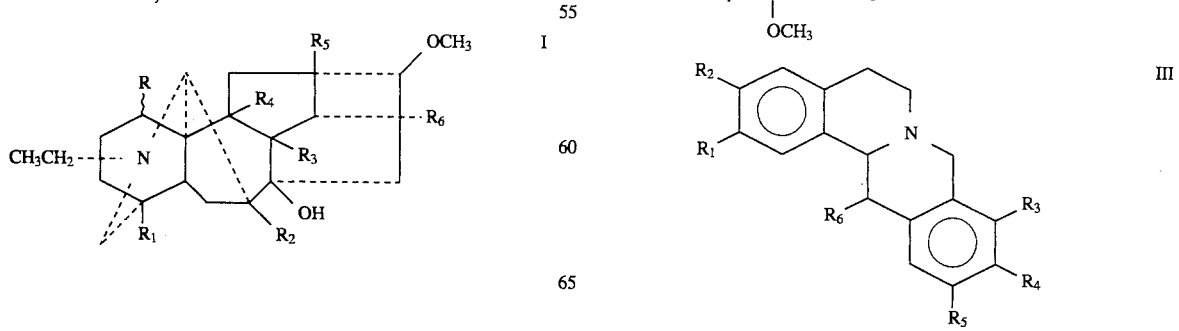

wherein in formula I
R=β-OCH₃, β-OH or α-OCH₃,
R₁=OAcABz, OH, OABz or H,
R₂=H or OH,
R₃=H or OH,
R₄=H or OH,
R₅=H or OH,
R₆=OCH₃, OBz, OAc or OH;

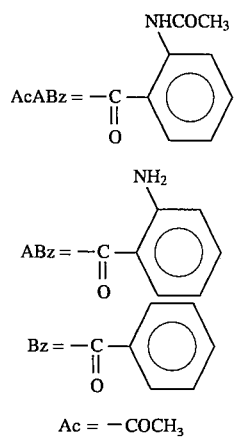

wherein in formula II,
R₁=R₂=R₃=OH; and in formula III,
R₁=OCH₃ or OH,
R₂=OCH₃,
R₃=OCH₃ or H,
R₄=OCH₃ or OH,
R₅=H or OCH₃,
R₆=H or CH₃ and a pharmaceutical excipient.

2. The composition of claim 1 in which the aconitane derivatives are lappaconitine or its inorganic acid salts.

3. The composition of claim 1 in which the aconitane derivatives are N-deacetyllappaconitine or its inorganic acid salts.

4. The composition of claim 1 in which the aconitane derivatives are lappaconine or its inorganic acid salts.

5. The composition of claim 1 in which the aconitane derivatives are aconine or its inorganic acid salts.

6. The composition of claim 1 in which the aconitane derivatives are the total alkaloids of Aconitum sinomontanum Nakai or its inorganic salts.

7. The composition of claim 1 in which said tetrahydroprotoberberine derivative is 1-tetrahydropalmatine.

8. The composition of claim 1 in which said tetrahydroprotoberberine derivative is dl-tetrahydropalmatine.

9. The composition of claim 1 in which said tetrahydroprotoberberine derivative is stepholidine.

10. The composition of claim 1 in which said tetrahydroprotoberberine derivative is corydaline.

11. The composition of claim 1 in which said tetrahydroprotoberberine derivative is xylopinine.

12. The composition of claim 1 which further contains an anticholinergic agent.

13. The composition of claim 12 wherein the anticholinergic agent is selected from the group consisting of scopolamine hydrobromide and anisodamine hydrobromide.

14. A composition comprising a compound selected from the group consisting of lappaconitine, lappaconine, N-deacetyllappaconitine, and the total alkaloid hydrobromides of Aconitum sinomontanum Nakai; a compound selected from the group consisting of l-tetrahydropalmatine, dl-tetrahydropalmatine sulfate, and stepholidine hydrobromide; and a compound selected from the group consisting of scopolamine hydrobromide and anisodamine hydrobromide and a pharmaceutical excipient.

15. A method for treating the withdrawal symptoms of drug addicts comprising administering an anti-withdrawal symptom effective amount of the composition of claim 1 to the drug addict.

16. A method for detoxifying a drug addict comprising administering a drug-detoxifying effective amount of the composition of claim 1 to the drug addict.

17. The method of claim 15 in which the composition is administered by oral route, subcutaneous injection, intramuscular injection or intravenous instillation.

18. The method of claim 16 in which the composition is administered by oral route, subcutaneous injection, intramuscular injection.

19. A method for treating the withdrawal symptoms of drug addicts comprising administering an anti-withdrawal symptom effective amount of the composition of claim 14 to the drug addict.

20. A method for detoxifying a drug addict comprising administering a drug-detoxifying effective amount of the composition of claim 14 to the drug addict.

21. The composition of claim 1 in which the aconitane derivatives are ranaconitine or its inorganic salts.

22. The composition of claim 1 in which the aconitane derivatives are N-deacetylranaconitine or its inorganic salts.

23. The composition of claim 1 in which the aconitane derivatives are N-deacetylfinaconitine or its inorganic salts.

24. The composition of claim 1 in which the aconitane derivatives are episcopalisinine or its inorganic salts.

25. The composition of claim 1 in which the aconitane derivatives are delavaconine or its inorganic salts.

26. The composition of claim 1 in which the aconitane derivatives are aconisine or its inorganic salts.

27. The composition of claim 1 in which the aconitane derivatives are scopaline or its inorganic salts.

* * * * *